United States Patent
Axelrod

(10) Patent No.: US 7,643,148 B2
(45) Date of Patent: Jan. 5, 2010

(54) APPARATUS AND METHOD FOR THE DETECTION OF MOLECULES

(75) Inventor: Noel Axelrod, Jerusalem (IL)

(73) Assignee: Physical Logic AG, Zug (CH)

( * ) Notice: Subject to any disclaimer, the term of this patent is extended or adjusted under 35 U.S.C. 154(b) by 99 days.

(21) Appl. No.: 12/112,533

(22) Filed: Apr. 30, 2008

(65) Prior Publication Data
US 2009/0116027 A1    May 7, 2009

Related U.S. Application Data

(60) Provisional application No. 60/914,804, filed on Apr. 30, 2007.

(51) Int. Cl.
*G01B 9/02* (2006.01)
*G01J 3/45* (2006.01)

(52) U.S. Cl. ........................... 356/454; 356/484

(58) Field of Classification Search ............... 356/451, 356/454, 484, 481, 517; 250/339.07, 339.08, 250/339.09
See application file for complete search history.

(56) References Cited

U.S. PATENT DOCUMENTS

| 6,977,379 B2 * | 12/2005 | Zhang et al. ............. 250/341.1 |
| 7,259,859 B2 * | 8/2007 | Pepper ....................... 356/451 |
| 7,352,466 B2 * | 4/2008 | Cao et al. ................... 356/437 |
| 7,459,687 B2 * | 12/2008 | Federici et al. .......... 250/341.8 |
| 2009/0212769 A1 * | 8/2009 | Stoica et al. ............. 324/244.1 |

* cited by examiner

*Primary Examiner*—Patrick J Connolly
(74) *Attorney, Agent, or Firm*—Edward S. Sherman

(57) ABSTRACT

A THz. spectrometer a includes an adjustable resonator situated between two parabolic mirrors at least one being movable with a stepper motor to create a resonance chamber. A terahertz source irradiated the chamber and a mixer which also receives a signal modulated by the sample in the resonance chamber.

7 Claims, 2 Drawing Sheets

APPARATUS AND METHOD FOR THE DETECTION OF MOLECULES

CROSS REFERENCE TO RELATED APPLICATIONS

The present application claims priority to U.S. provisional patent application having Ser. No. 60/914,804 for a "APPARATUS AND METHOD FOR THE DETECTION OF MOLECULES", filed on Apr. 30, 2007, which is incorporated herein by reference

BACKGROUND OF INVENTION

This invention relates generally to the fields of molecular physics and material detection, and more specifically on the physical concept of molecular rotational frequencies in order to detect the presence of specific molecules of interest.

Current material detection solutions rely either upon what is known as "sniffers" or on optically-based technologies. Sniffers are systems that can detect the presence of specific materials. This is done by using a cantilever sensor (usually a MEMS cantilever) with a tip which only reacts to a specific type of material. An example of a sniffer is the gate at airports where an air current is blown at the person standing within the gate. Molecules dislodged as a result of the air current are blown through an air conductor with a cantilever inside of it. As stated, the cantilever only reacts to a specific type of material. Once a molecule (or molecules) of the material touch the tip of the cantilever they change the resonance frequency of that cantilever. The difference between the original resonance frequency and the current resonance frequency allows one to "know" that the specific material has been detected and to act upon this knowledge.

Sniffer systems suffer from the following disadvantages:

Accuracy of detection—the ability of the system to detect the presence of a material is highly dependent upon its concentration in the sampled area. Since such a system relies upon the existence of residual amounts of the illicit material; the farther it is from the source the less accurate it is.

Limited in types of materials it can detect—the system relies upon the concept of the cantilever sensor, where the tip is treated to react to a specific material. This limits the range of materials that can be recognized.

Optical systems rely upon the "rotational frequency" effect in molecules. A beam of light at a specific wavelength (frequency) is transmitted to a specific target area. When the light at that specific wavelength excites the material of interest, the reflected light will be at a different wavelength (usually double that of the original transmitted wavelength). By knowing when the original light was transmitted and knowing that only this transmission is what has caused the detection of a new wavelength, one can ascertain that the material of interest is present. An example of the way this system is used is when a swab is passed over baggage and inserted in a sealed box. Within this box the light at a specific wavelength is directed at the sample and the existence of illicit materials is thus confirmed if a specific shift in wavelength is detected.

The main limitations of the systems that rely upon the "rotational frequency" effect are that they require some sort of physical contact with the sample. An additional drawback is that the amount of energy required to correctly trigger the "rotational frequency" effect must be quite precise; using too little or too much energy will not provide the necessary result for the analysis.

It is therefore a first object of the present invention to provide an improved means for spectral analysis of unknown materials that overcomes the aforementioned and other disadvantages of the prior art.

Embodiments of the present invention alleviating some of these disadvantages will now be described. Embodiments of the present invention can use a terahertz (THz) signal generator for the analysis of molecules in a sample. The analysis can use a chamber that can be made very small relative to current systems, however, it should be clear to a person skilled in the art that the chamber can be made whatever size suits the needs of the specific application. The present system does not require any physical contact with the molecules it analyzes, and can detect minute concentrations of a material of interest.

Additional features and advantages of the invention will become apparent to those skilled in the art upon consideration of the following detailed description of illustrated embodiments.

SUMMARY OF INVENTION

In the present invention a method of Fourier Transform THz Spectroscopy comprises the steps of: providing a resonance cavity having first mirror and the second mirror at opposing ends, with a mixer and a THz source in signal communication with the resonance cavity and the mixer, placing a sample to be analyzed in the resonance cavity, generating a THz signal by the THz source, whereby the generated THz signal is input to the resonance cavity and the mixer, combining the output signal from the chamber with the input signal at the mixer to form a mixed signal at a first resonant frequency of the cavity, varying the distance between the first mirror and the second mirror to changes the resonant frequency of the cavity, acquiring the mixed signal at a plurality of resonant frequencies defined by the distance between the first and second mirrors to obtain a spectral response from the sample, analyzing the acquired spectral response to determine the presence of particular molecular species in the sample.

The above and other objects, effects, features, and advantages of the present invention will become more apparent from the following description of the embodiments thereof taken in conjunction with the accompanying drawings.

BRIEF DESCRIPTION OF THE DRAWINGS

Aspects of the present invention are more particularly described below with reference to the following figures, which illustrate exemplary embodiments of the present invention.

DETAILED DESCRIPTION

Figure 1:
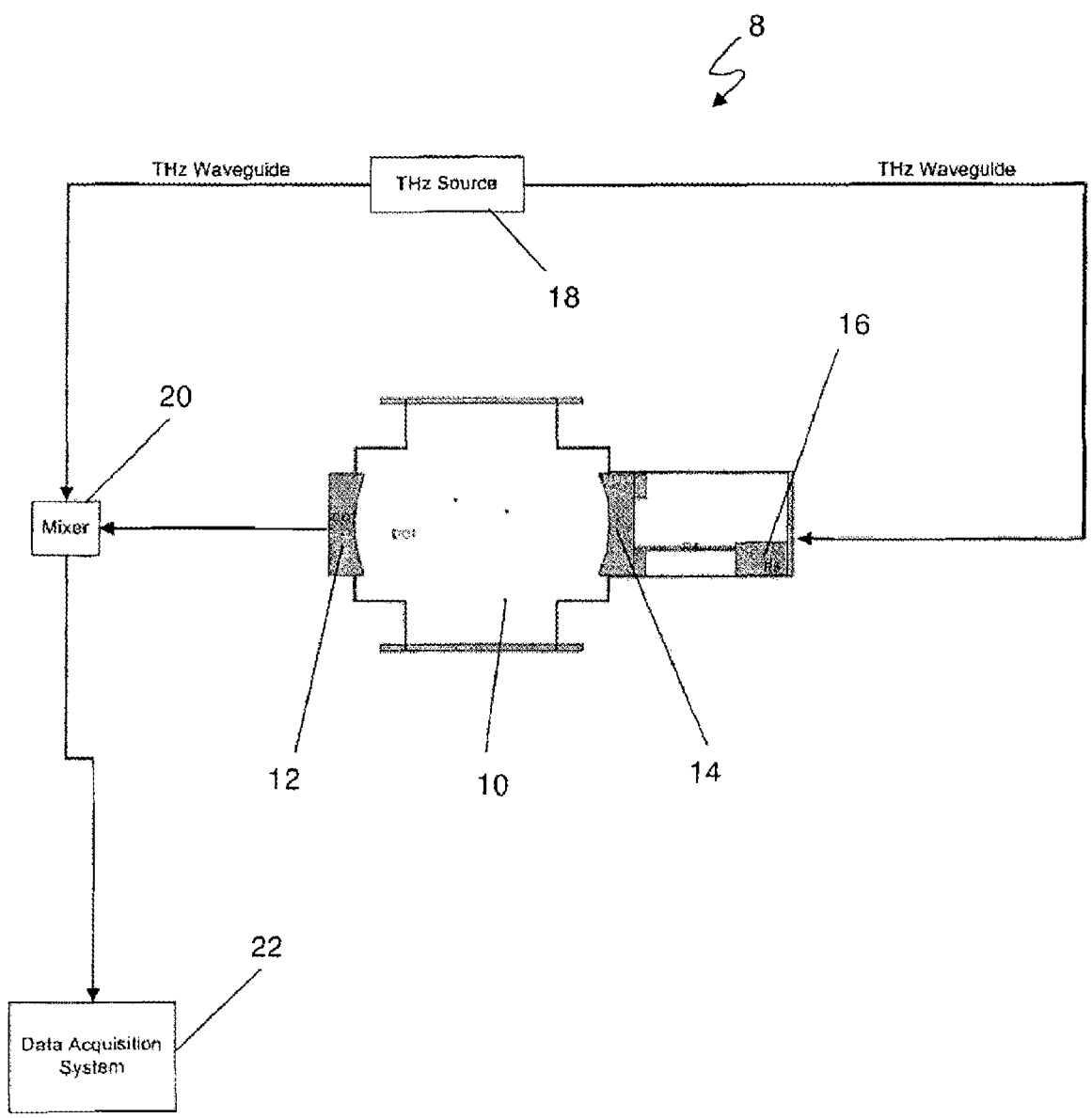
FIG. 1 is a schematic diagram of an embodiment of a system for spectrum analysis; and, FIG. 2 is a flow chart of a method using the embodiment of FIG. 1 to determine the concentration of molecules of interest.
Figure 2:
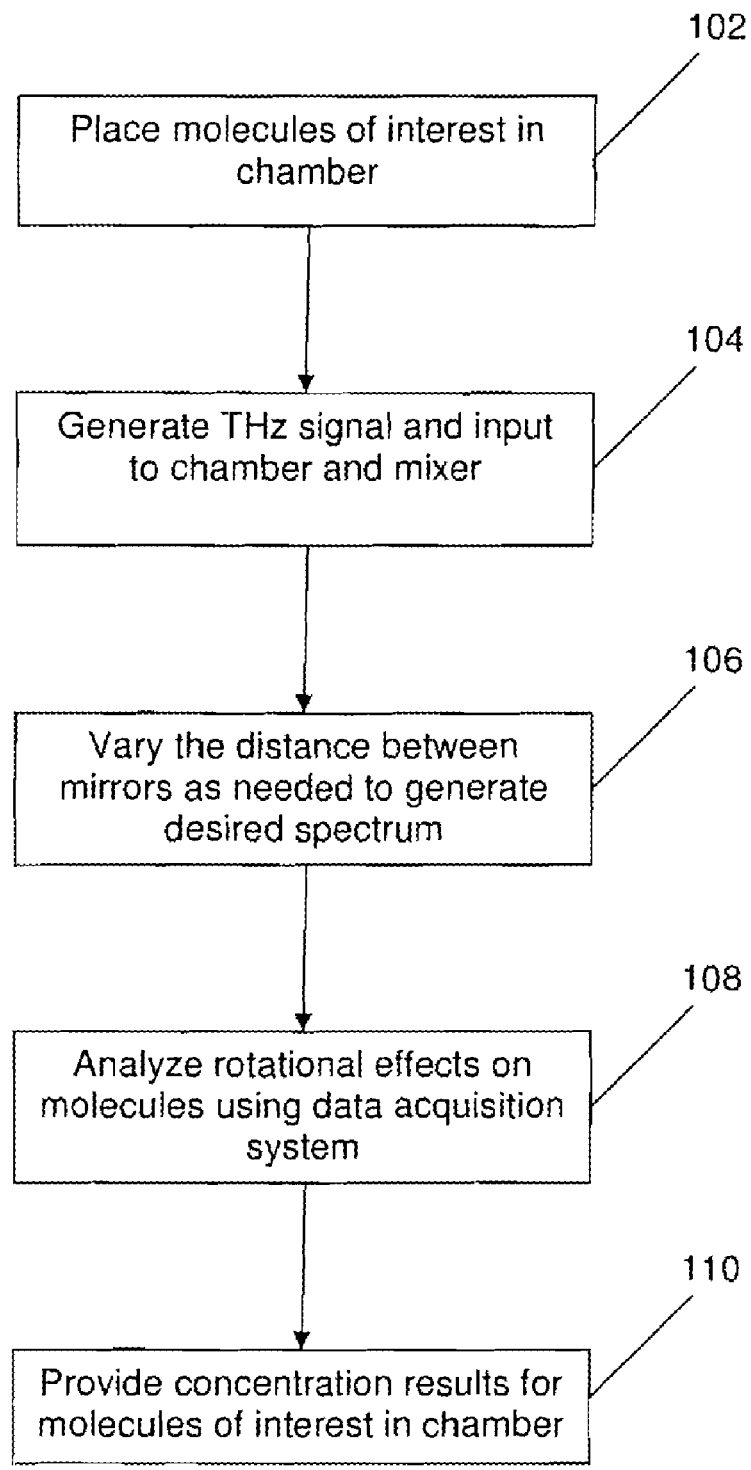

Referring to FIGS. 1 through 2, wherein like reference numerals refer to like components in the various views, there is illustrated therein a new and improved APPARATUS AND METHOD FOR THE DETECTION OF MOLECULES generally denominated 8 herein.

The spectrum of organic molecules is very complex, and is divided into electronic states inside the atom: vibrational states, rotational states and spin states. Rotational states are usually smaller than vibrational states. The rotational line frequency formula is:

$$v = 2B(J+1) \quad (1)$$

Where B is in the order of $6 \times 10^{10}$ Hz. and J is the angular momentum of the molecule. The rotational spectrum lies in either the microwave absorption region or the terahertz (THz) range.

system does not require any physical contact with the molecules it analyzes, and can detect minute concentrations of a material of interest.

Additional features and advantages of the invention will become apparent to those skilled in the art upon consideration of the following detailed description of illustrated embodiments.

The rotational spectrum provides us with a unique "fingerprint" of the molecule that can unambiguously identify a molecule of interest.

One of the ways to determine the rotational spectrum of molecules in specific mediums (such as air, liquid etc) is to use Fourier Transform Microwave Spectroscopy (FTMS).

FIG. 1 shows an embodiment of a system for spectrum analysis 8 that includes an adjustable resonator 10 situated between two parabolic mirrors (or cavity mirrors) 12, 14, and also includes a step motor 16, a terahertz source 18 and a mixer 20. The two parabolic mirrors 12, 14 create a resonance chamber. The step-motor 16 can change the distance between the first parabolic mirror 12 and the second parabolic mirror 14 which produces a change of the resonant frequency and effectively creates a scanning system.

Terahertz sources for use in the invention are known in the art, such as those described in U.S. Pat. Nos. 7,274,147 (Issued to Shim, et al. on Sep. 25, 2007); 7,113,534 (issued to Unterrainer, et al. on Sep. 26, 2006) and 6,144,679 (issued to Herman, et al. on Nov. 7, 2000), all of which are incorporated herein by reference. Further, Terahertz detectors are described in U.S. Pat. No. 7,242,010 (issued to Liu, et al. on Jul. 10, 2007) as well as 7,230,244 (issued to Trotz, et al. on Jun. 12, 2007), both of which are also incorporated herein by reference.

The THz source 18 transmits a signal into both the resonance chamber 10 and the mixer 20 at the same time. An output signal is obtained from the resonance chamber 10 using one of the mirrors 12, 14 and is also fed into the mixer 20. The mixer 20 can be a Schottky diode. The combined result of the signal from the THz source 18 and the output signal from the resonance chamber 10 after passing through the mixer 20 is then fed into a data acquisition system 22 where it is processed and analyzed. It will be obvious to those of ordinary skill in the art that the spectrum analysis system 8 can be used with various types of data acquisition systems 22 to determine the presence of materials of interest.

The size of the resonance chamber 10 (i.e. the distance between the first mirror 12 and the second mirror 14) can be in the single centimeter (cm) range, and the size can be increased or decreased depending on the requirements of the application. The size can be calculated from the following formula:

$$L = \frac{\lambda}{2} n \quad (2)$$

Where $\lambda$ is the wavelength of the signal and n is an integer. For example, if we take a signal with a frequency of 1 THz, the wavelength is approximately 0.3 mm ($\lambda = c/f$), and a value of n equal to 100, then L would be 1.5 cm. Changing the value of L will change the resonant frequency inside the cavity allowing the performance of a Fourier Spectral Analysis.

It should be apparent to someone skilled in the art that by changing the value of L we can change the size of the cavity chamber 10, therefore changing the overall size of the system 8, from a small device which optionally can be handheld, to a room sized device. In a room sized device, the two mirrors 12, 14 (in a larger scale of meters for example) can be positioned on opposite walls of the room and anything passing between them actually passes through the cavity chamber 10.

A method for using the embodiment shown in FIG. 1 can include the steps shown in FIG. 2. At step 102, the sample molecules are placed in the resonance chamber 10. The resonance chamber 10 does not need to be a vacuum, and can be filled with air.

At step 104, a THz signal is generated by the source 18 and input to the resonance chamber 10 and the mixer 20.

At step 106, the motor 16 is used to vary the distance between the first mirror 12 and the second mirror 14 which changes the resonant frequency of the cavity 10. For the different resonant frequencies, the output signal from the chamber 10 is combined in the mixer 20 with the input signal from the THz source 18, and the mixed signal is input to the data acquisition system 22.

At step 108, the data acquisition system 22 analyzes the output signals from the mixer 10 for the different resonant frequencies to determine the rotational effects on the molecules in the resonance chamber 10.

At step 110, the data acquisition system 22 provides a reading for the concentration of the molecules of interest in the chamber 10.

The sensitivity of this system is extremely high due to a high-Q cavity. An additional advantage of this system is that it does not require the use of a vacuum as needed in some similar systems.

An advantage of this Fourier Transform THz Spectroscopy System is that it allows an unambiguous species identification, in addition to its high resolution and sensitivity as described above coupled with its ability to detect nearly single molecules in the cavity.

Exemplary embodiments of the present invention have been shown by way of example in the drawings and are herein described in detail; however the present invention is susceptible to various modifications and alternative forms. It should be understood that there is no intent to limit the system to the particular forms disclosed, but on the contrary, the intention is to address all modifications, equivalents, and alternatives falling within the spirit and scope of the system as defined herein that would occur to one skilled in the art.

The invention claimed is:

1. A method of Fourier Transform THz Spectroscopy comprising the steps of:
   a) providing a resonance cavity having first parabolic mirror facing a second parabolic mirror at opposing ends thereof, with a THz. signal mixer and a THz source in signal communication with the resonance cavity and the mixer,
   b) placing a sample to be analyzed in the resonance cavity,
   c) generating a THz signal by the THz source, whereby the generated THz signal is input to the resonance cavity and the mixer,
   d) combining the output signal from the chamber with the input signal at the mixer to form a mixed signal at a first resonant frequency of the cavity, e) varying the distance between the first mirror and the second mirror to changes the resonant frequency of the cavity, f) acquiring the mixed signal at a plurality of resonant frequencies defined by the distance between the first and second mirrors to obtain a spectral response from the sample, g) analyzing the acquired spectral response to determine the presence of particular molecular species in the sample.

2. A method of Fourier Transform THz Spectroscopy according to claim 1 further comprising the step of determining the concentration of one or more particular molecular species in the sample.

3. A method of Fourier Transform THz Spectroscopy according to claim 1 wherein the mixer is a Schottky diode.

4. A method of Fourier Transform THz Spectroscopy according to claim 1 wherein the cavity is at least partly evacuated prior to placing the sample in the resonance cavity.

5. A method of Fourier Transform THz Spectroscopy according to claim 2 wherein the mixer is a Schottky diode.

6. A method of Fourier Transform THz Spectroscopy according to claim 2 wherein the cavity is at least partly evacuated prior to placing the sample in the resonance cavity.

7. A method of Fourier Transform THz Spectroscopy according to claim 4 wherein the cavity is at least partly evacuated prior to placing the sample in the resonance cavity.

* * * * *